(12) United States Patent
Hardy

(10) Patent No.: US 12,734,318 B2
(45) Date of Patent: Sep. 15, 2026

(54) ASSEMBLY FOR SECURING EXPOSED DOSE ADJUSTMENT CONTROL MECHANISMS OF MEDICAL DEVICES USED TO ADMINISTER VARIOUS MEDICAL THERAPIES

(71) Applicant: ServiceNet, Inc., Northampton, MA (US)

(72) Inventor: Robert Hardy, Belchertown, MA (US)

(73) Assignee: ServiceNet, Inc., Northampton, MA (US)

( * ) Notice: Subject to any disclaimer, the term of this patent is extended or adjusted under 35 U.S.C. 154(b) by 0 days.

(21) Appl. No.: 19/375,381

(22) Filed: Oct. 31, 2025

(65) Prior Publication Data

US 2026/0124411 A1 May 7, 2026

Related U.S. Application Data

(60) Provisional application No. 63/716,857, filed on Nov. 6, 2024.

(51) Int. Cl.
*A61M 16/00* (2006.01)

(52) U.S. Cl.
CPC . *A61M 16/0003* (2014.02); *A61M 2202/0208* (2013.01)

(58) Field of Classification Search
CPC .................. A61M 16/0003; A61M 2202/0208
USPC .................................................... 70/158, 232
See application file for complete search history.

(56) References Cited

U.S. PATENT DOCUMENTS 1,944,535 A * 1/1934 White ................ B60K 15/0409 70/164
2,048,424 A * 7/1936 Caldwell ............... F16L 19/005 285/80
2,656,706 A * 10/1953 Lucas .................. B62D 53/085 280/434

(Continued)

FOREIGN PATENT DOCUMENTS

CN 210355579 4/2020
CN 211024627 7/2020

(Continued)

OTHER PUBLICATIONS

International Search Report issued in corresponding International Application No. PCT/US2025/053916 on Mar. 4, 2026.

(Continued)

*Primary Examiner* — Kristina R. Fulton
*Assistant Examiner* — James Edward Ignaczewski
(74) *Attorney, Agent, or Firm* — Bulkley, Richardson and Gelinas, LLP; Mary R. Bonzagni, Esq.

(57) ABSTRACT

An assembly and method for housing and securing exposed dose adjustment control mechanisms of medical devices used to administer various medical therapies, is provided. In an exemplary embodiment, the inventive assembly and method serve to house and secure exposed dose adjustment control mechanisms of oxygen concentrators used to provide oxygen therapy. The inventive assembly, which securely encloses a dose adjustment control mechanism, permitting access only to select individuals, is made up of a cup-shaped hollow member having a through-hole in a distal wall, and a lid. The cup-shaped hollow member and the lid are held together by a hinge or fastening means, and fastening/locking means.

26 Claims, 5 Drawing Sheets

(56) References Cited

U.S. PATENT DOCUMENTS 3,126,243 A * 3/1964 Manetti et al. .... H01R 33/7664 439/135
3,349,947 A * 10/1967 Zumwalt ............. F16L 55/1018 220/361
4,073,165 A 2/1978 Grundstrom et al.
5,779,074 A * 7/1998 Burns ................. B01L 3/50825 215/296
6,272,890 B1 8/2001 Huston
6,367,293 B1 * 4/2002 Elliott ................... E05B 67/383 70/57
6,880,368 B1 * 4/2005 Ulbrich .................... B60D 1/06 280/425.2
7,178,546 B2 * 2/2007 Gremillion, III ....... F16K 35/10 137/15.01
8,353,309 B1 * 1/2013 Embry ................... A62C 35/20 70/164
2003/0066166 A1 * 4/2003 Gremillion, III ....... F16K 35/10 16/413
2010/0107708 A1 * 5/2010 Kolton .................... B60R 25/09 70/226
2022/0228400 A1 7/2022 Remiz

FOREIGN PATENT DOCUMENTS

CN 217246006 8/2022
CN 117563093 A1 2/2024
KR 20230111587 A * 7/2023 ........ A61M 16/1065
TW M380136 U * 5/2010
WO 2020222722 A1 11/2020

OTHER PUBLICATIONS

Written Opinion of the International Searching Authority issued in corresponding International Application No. PCT/US2025/053916 on Mar. 4, 2026.

* cited by examiner

ASSEMBLY FOR SECURING EXPOSED DOSE ADJUSTMENT CONTROL MECHANISMS OF MEDICAL DEVICES USED TO ADMINISTER VARIOUS MEDICAL THERAPIES

CROSS-REFERENCE TO RELATED APPLICATION

This application claims the benefit of priority of U.S. Provisional Patent Application Ser. No. 63/716,857, filed Nov. 6, 2024, the contents of which are herein incorporated by reference.

TECHNICAL FIELD

The present invention generally relates to an assembly and method for housing and securing exposed dose adjustment control mechanisms of medical devices used to administer various medical therapies, and in an exemplary embodiment relates to an assembly and method for housing and securing exposed dose adjustment control mechanisms of oxygen concentrators used to provide oxygen therapy. The term “control mechanism”, as used herein, includes a user-actuatable element, such as a knob, dial, or other rotary or slidable control configured to adjust the quantity of a medicine or drug (e.g., medical-grade oxygen) being administered by the device.

BACKGROUND

A number of different types of medicament dispensers for dispensing various types of medicines or drugs to patients have been suggested in the past. The type and amount of dispensed medicine or drug is set by a qualified healthcare provider. Dispensers with exposed dose adjustment control mechanisms, which can be either inadvertently or intentionally altered, present a risk to the patient.

One such medicine or drug is medical-grade oxygen. Supplemental oxygen therapy is used for those who frequently experience low oxygen levels including people with COPD, COVID-19, emphysema, sleep apnea and other breathing problems. Low blood oxygen levels (hypoxemia) can damage organs and be life-threatening.

There are several types of oxygen therapy systems, which may be large and stationary for home use, or small and portable. One such oxygen therapy system is an oxygen concentrator. Oxygen concentrators are devices that remove nitrogen and other gases from air and deliver purified oxygen to a user. Oxygen concentrators are recognized as the easiest portable system to travel with.

As alluded to above, medical-grade oxygen is a medicament or medication and requires a prescription from a qualified healthcare provider. They will prescribe oxygen at a specific flow rate to use at rest, during activity, and during sleep. Once the prescribed flow rate is set on an oxygen concentrator, intentional or accidental tampering with the set flow rate may cause health risks. Too little oxygen can put a strain on a patient’s heart and brain, causing heart failure, fatigue or memory loss, while too much can cause some patients to slow their breathing to dangerously low levels.

The present invention serves to address the risks caused by intentional or accidental tampering with settings on medical devices used to administer various medical therapies.

SUMMARY

In particular, the present invention provides an assembly for housing and securing exposed dose adjustment controls of medical devices used to administer various medical therapies. In one contemplated embodiment, the inventive assembly houses and secures exposed dose adjustment control mechanisms of oxygen concentrators used to administer oxygen therapy.

Once the inventive assembly is in place on a medical device, the assembly prevents access to a dose adjustment control mechanism. The inventive assembly comprises a cup-shaped hollow member having a through-hole in a distal wall, and a lid. The cup-shaped hollow member and the lid are held together by a hinge or fastening means, and fastening/locking means.

In a first exemplary embodiment, the inventive assembly is either a one-piece or a two-piece assembly, wherein the cup-shaped hollow member and the lid are connected by a hinge (e.g., a living hinge or a mechanical hinge), which allows for bending of the lid from an ‘open’ position removed from the cup-shaped hollow member to a ‘closed’ position on and in alignment with the cup-shaped hollow member. As will be explained in more detail below, once the inventive assembly is in place on a medical device, the device’s dose adjustment control mechanism set, and the lid positioned to a ‘closed’ position, the lid may be secured in place by electronic fastening/locking means, or by mechanical fastening/locking means such as a lock and key.

In a second exemplary embodiment, the inventive assembly is a two-piece assembly, wherein the cup-shaped hollow member and the lid are connected by fastening means (e.g., a bolt (secured by a nut)), which allows for rotation of the lid (e.g., rotation of the lid around the bolt shaft) from an ‘open’ position on but misaligned or moved away from an aligned position with the cup-shaped hollow member to a ‘closed’ position on and in alignment with the cup-shaped hollow member. As mentioned above, once the inventive assembly is in place on a medical device, the device’s dose adjustment control mechanism set, and the lid positioned to a ‘closed’ position, the lid may be secured in place by electronic fastening/locking means, or by mechanical fastening/locking means such as a lock and key.

The present invention further provides a method for housing and securing exposed dose adjustment control mechanisms of medical devices using the inventive assembly, which includes a cup-shaped hollow member having a through-hole in a distal wall, and a lid, wherein the cup-shaped hollow member and the lid are held together by a hinge or fastening means, and fastening/locking means, wherein each dose adjustment control mechanism includes a user-actuatable element (e.g., a knob, dial, or other rotary or slidable control), wherein the method comprises:

- (a) removing the user-actuatable element from a stem (e.g., a screw stem) on a medical device used to administer various medical therapies;
- (b) positioning the cup-shaped hollow member’s through-hole over the stem;
- (c) replacing the user-actuatable element by placing it back onto the stem;
- (d) setting a prescribed quantity of a medicine or drug using the user-actuatable element; and
- (e) bending or rotating the lid onto and in alignment with the cup-shaped member and then securing the lid in place on the cup-shaped hollow member, thereby preventing access to the user-actuatable element.

In an exemplary embodiment, the method is for housing and securing an exposed dose adjustment control mechanism, which includes a user-actuatable element, on an oxygen concentrator using the inventive assembly described above, and comprises:

(a) removing the user-actuatable element from a stem on the oxygen concentrator;

(b) positioning the cup-shaped hollow member's through-hole over the stem;

(c) replacing the user-actuatable element by placing it back onto the stem;

(d) setting the oxygen flow rate using the user-actuatable element; and (e) bending or rotating the lid onto and in alignment with the cup-shaped hollow member and then securing the lid in place on the cup-shaped hollow member, thereby preventing access to the user-actuatable element.

Other features and advantages of the invention will be apparent to one of ordinary skill from the following detailed description and accompanying drawings.

Unless otherwise defined, all technical and scientific terms used herein have the same meaning as commonly understood by one of ordinary skill in the relevant art(s). All publications, patent applications, patents and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

The present disclosure may be better understood with reference to the following drawings. Components in the drawings are not necessarily to scale, emphasis instead being placed upon clearly illustrating the principles of the present disclosure.

Particular features of the disclosed invention are illustrated by reference to the accompanying drawings of the following exemplary embodiments of the present invention.

DETAILED DESCRIPTION

As previously noted, the present invention serves to address the risks caused by intentional or accidental tampering with settings on medical devices used to administer various medical therapies. Such medical devices include, but are not limited to, oxygen therapy systems such as oxygen concentrators, which have exposed dose adjustment control mechanisms.

In an exemplary embodiment, the present invention addresses the risks caused by tampering with dose adjustment knobs of oxygen concentrators. These knobs fit onto stems for adjusting flow, pressure, etc. Exemplary knobs are selected from the group of: internal threaded knobs (i.e., knobs that screw directly onto a male stem); external threaded knobs (i.e., knobs that have a male thread that fits a female stem); set screw knobs (i.e., knobs having a small inside screw for securing it to a stem); push-on/snap-fit knobs (i.e., knobs with built-in locking features that engage with corresponding features on a stem).

Figure 1:
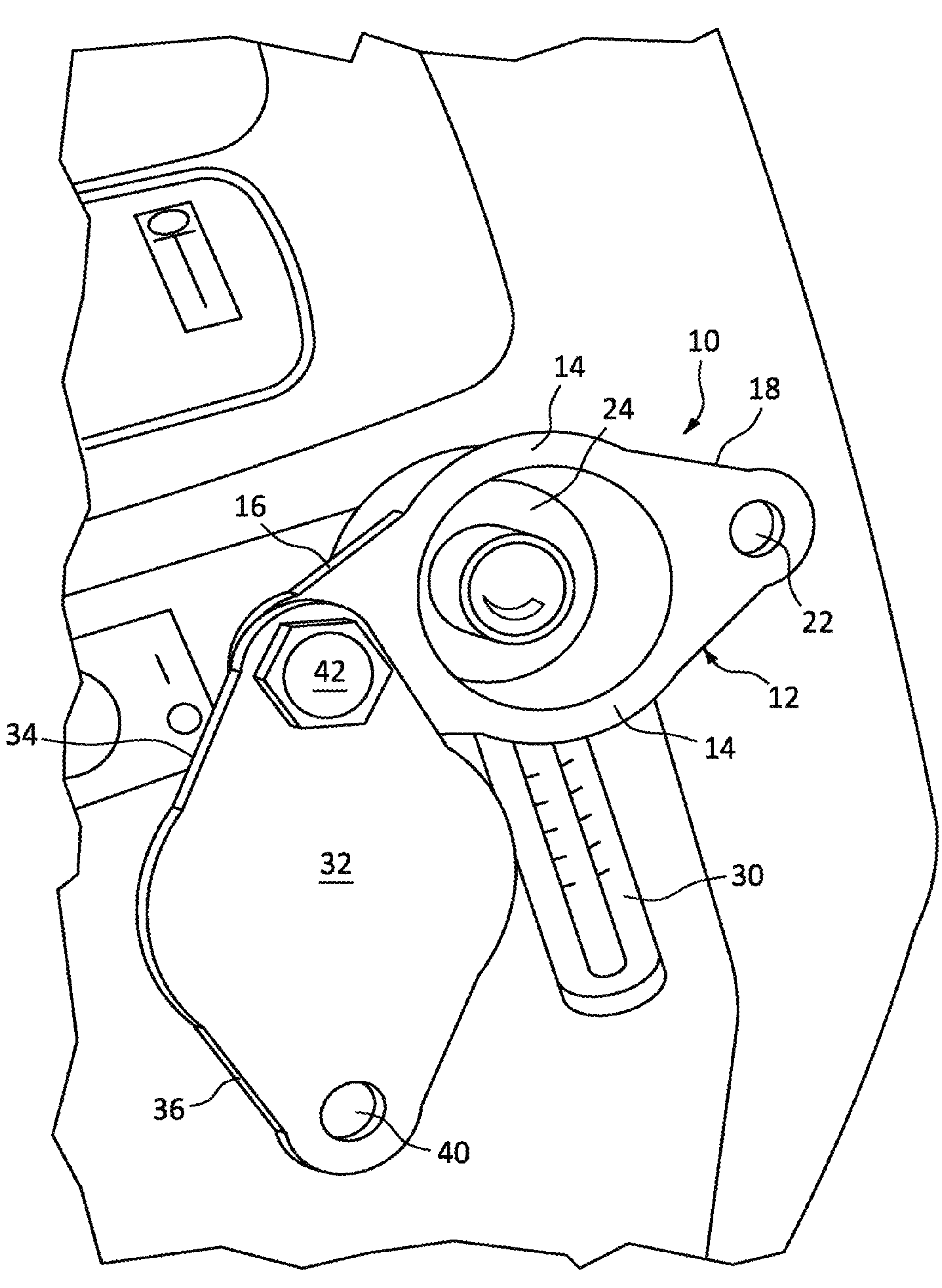
FIG. 1 is a perspective view of the inventive assembly in which the lid is partially attached to the upper rim of the cup-shaped hollow member or housing thereby exposing a dose adjustment knob of the oxygen concentrator.
Figure 2:
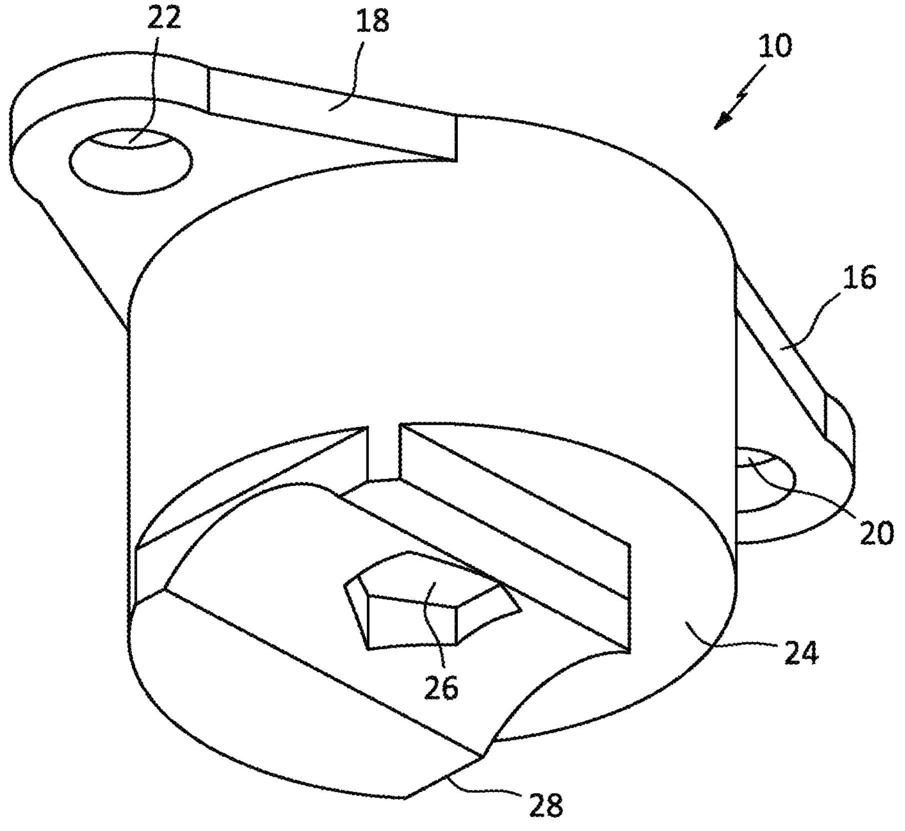
FIG. 2 is a perspective view of the base and base extension of the cup-shaped hollow member or housing of the inventive assembly with an hexagonal shaped through-hole.

As noted above, the inventive assembly may take the form of either a one-piece or a two-piece assembly. Referring now to the drawings in detail, an exemplary embodiment of the inventive two-piece assembly is shown generally at 10. As best shown in FIGS. 1 and 2, the inventive assembly 10 generally comprises a cup-shaped hollow member or housing 12 with an upper rim 14 having two oppositely extending arms 16, 18, each with a through-hole 20, 22, at a distal end. The one-piece assembly (not shown) has one through-hole at the distal end of one extending arm of the upper rim of the housing, the other distal end having a hinge attached or integrally formed thereon, which connects the housing to the lid. The hinge allows the lid to adopt both an 'open' position and a 'closed' position relative to the housing.

The hollow member or housing 12 has a base 24, and a base extension 28 off the base that is molded integrally therewith. A through-hole 26 extends through both the base 24 and the base extension 28 and may adopt any shape but preferably adopts the shape of the fastening means securing the screw stem 50 (FIG. 3) to the concentrator, which in this embodiment is an hexagonal nut. The base extension 28 conforms to the shape of the flow gauge 30 and adjoining surface of the oxygen concentrator allowing the housing 12 to lie flush or level with the surface of the concentrator.

The inventive assembly 10 further comprises a lid 32 substantially matching the overall size and shape of the upper rim 14 of the hollow member or housing 12. The lid 32 may be a separate component, which is connected to the housing 12 by way of either fastening means or a mechanical hinge, or it may form an integral part of the inventive assembly (i.e., the lid being connected to the housing 12 by way of a living hinge). For the inventive two-piece assembly shown in the drawings, fastening means in the form of a bolt 42 (secured by a nut), which allows for rotation around, for example, a shoulder screw, shoulder bolt, or stripper bolt, is permanently positioned in though-holes 20, 38 (not shown), thereby allowing the lid to swivel between an 'open' and 'closed' position on the two-piece assembly. The lid 32 has two oppositely disposed extending arms 34, 36, each with a through-hole 38 (not shown), 40, which align with through-holes 20, 22, respectively, when the lid is placed on top of the upper rim 14 of housing 12. For the inventive one-piece assembly in which the lid is connected to the housing 12 by way of a living hinge, the lid would only require one through-hole. When the lid is in a 'closed' position the one through-hole would align with the one through-hole on the upper rim of the housing. Once in place, fastening/locking means are placed through the aligned through-holes to secure the lid in place. Suitable fastening/locking means include mechanical or electronic fastening/locking devices. Once set to administer a medical therapy, the dose adjustment knob of the medical device shown in the drawings is secured by the inventive assembly by positioning a mechanical fastening/locking device (i.e., lock 44 shown in FIG. 5) in through-holes 22, 40, and then secured by locking the mechanical fastening/locking device, and while the medical device is not in use, the mechanical fastening/locking device is released or unlocked and then removed, and the lid positioned to an 'open' position to allow access to the dose adjustment knob.

In a preferred embodiment, the assembly is a one-piece or two-piece, molded plastic assembly. Molding of the assembly may be performed, for example, by injection molding, injection compression molding, compression molding, reaction injection molding (RIM) or foaming. The plastic may be selected from the group including polycarbonate resins, acrylic polymers, polyesters, polysulfone resins, and a combination comprising at least one of the foregoing. In an exemplary embodiment, the assembly is prepared using an opaque or heavily colored plastic that serves to obscure visual access to the dose adjustment knob.

The inventive assembly is sized to accommodate and secure the dose adjustment control mechanism of a medical device used to administer various medical therapies. In the exemplary embodiment shown in the drawings, the inventive two-piece assembly is used on an oxygen concentrator and when arranged in a 'closed' position has dimensions including a maximum length extending along the entire length of the lid ranging from about 50 millimeters (mm) to about 55 mm, a maximum width extending across the midpoint of the lid ranging from about 88 mm to about 90 mm, and a maximum height extending from an upper surface of the lid to the lowermost surface of the base extension ranging from about 40 mm to about 50 mm. The inner diameter of the cup-shaped member or housing ranges from about 40 mm to about 45 mm, while the inner height of the housing ranges from about 35 mm to about 40 mm. The thickness of the lid ranges from about 4 mm to about 6 mm, while the wall thickness of the housing ranges from about 2 mm to about 4 mm.

Figure 3:
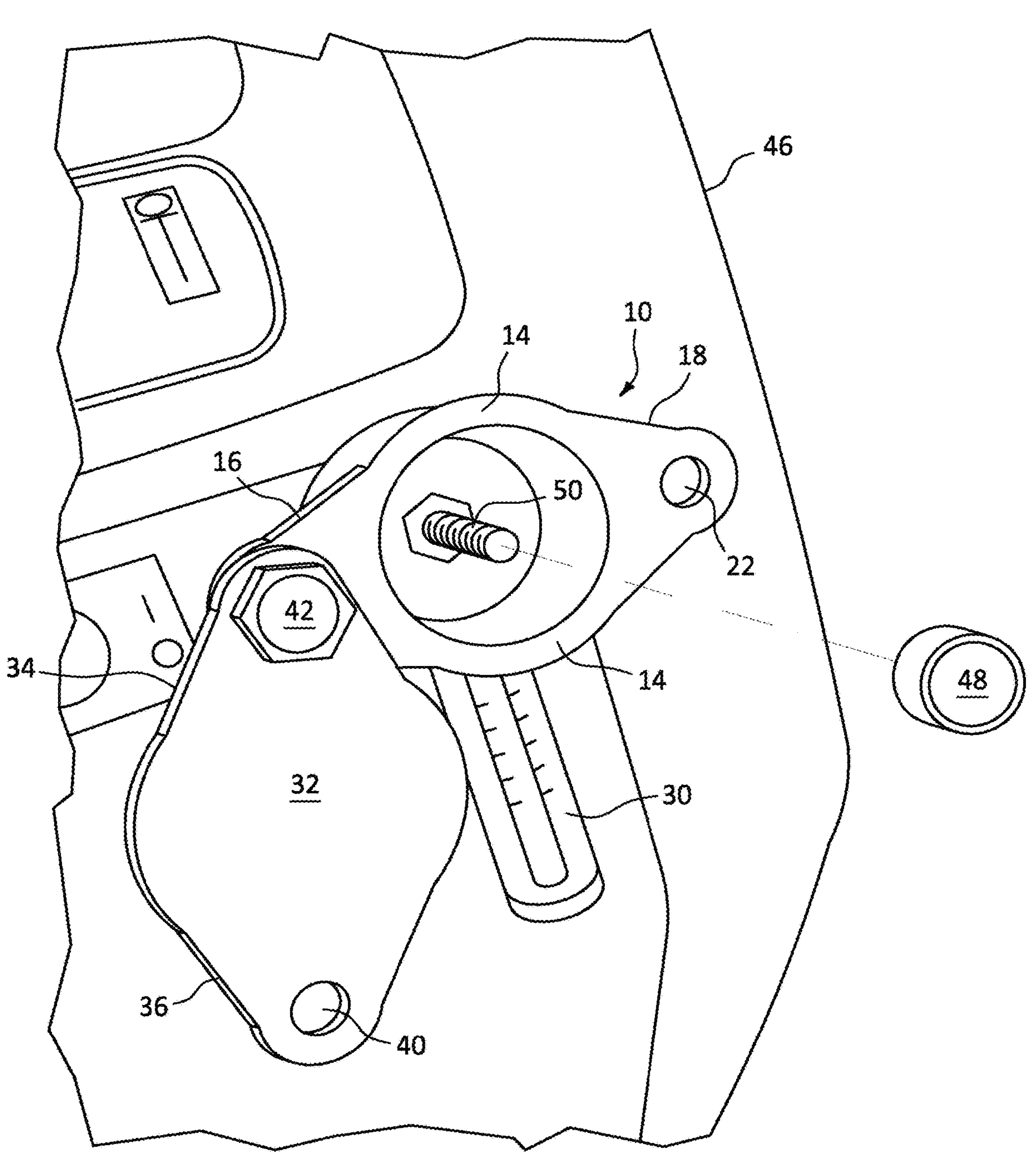
FIG. 3 is a perspective exploded view of the inventive assembly shown in FIG. 1 in which the dose adjustment knob has been removed from the screw stem and the cup-shaped hollow member or housing has been placed over the screw stem against the flow gauge of the oxygen concentrator.
Figure 4:
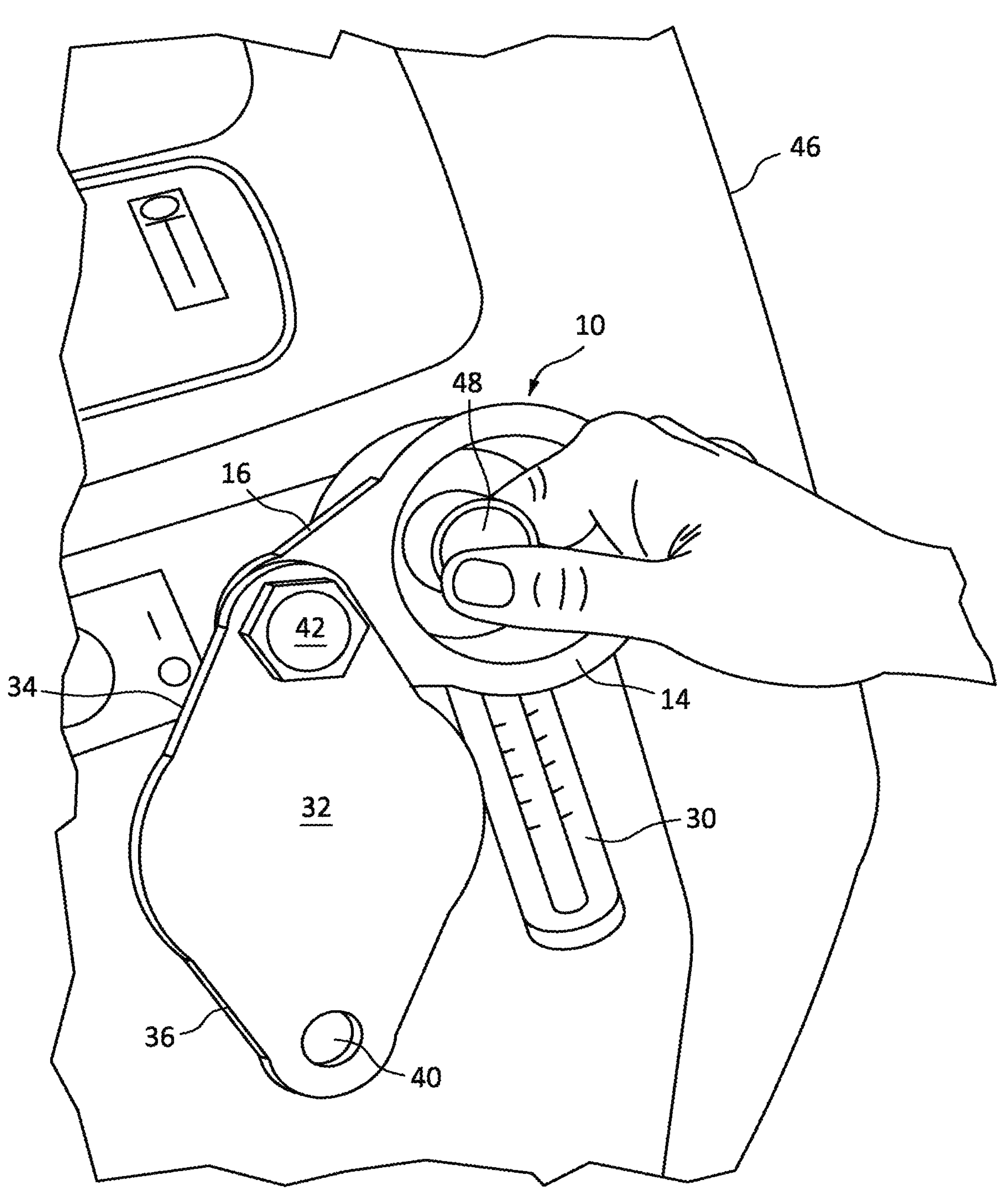
FIG. 4 is a perspective view of the inventive assembly shown in FIG. 3 in which the dose adjustment knob has been replaced back on the screw stem.
Figure 5:
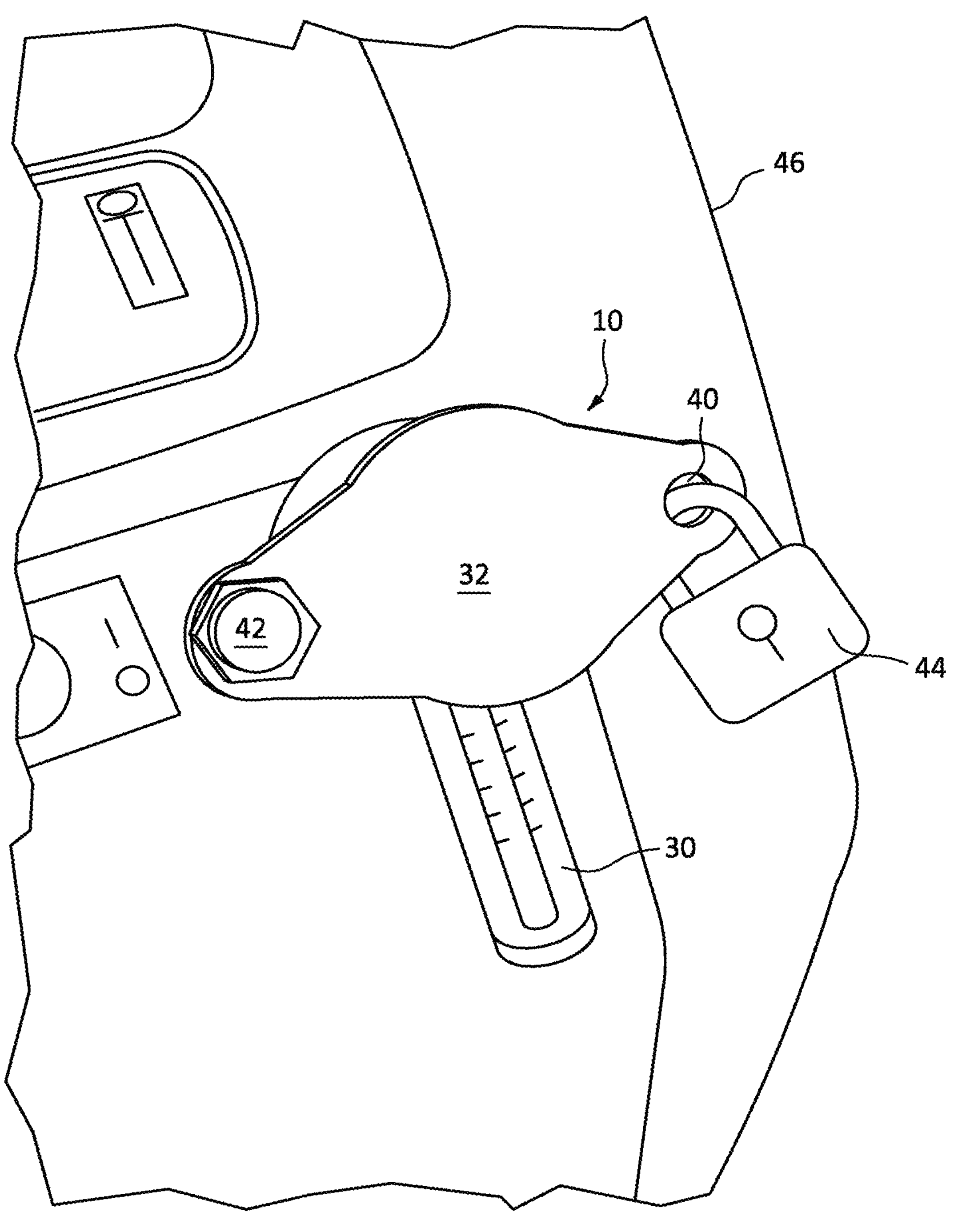
FIG. 5 is a perspective view of the inventive assembly in which the lid is shown secured to the cup-shaped hollow member or housing thereby preventing visual and physical access to the dose adjustment knob of the oxygen concentrator.

As best shown in FIGS. 3-5, during installation of the inventive two-piece assembly 10 on an oxygen concentrator 46, the dose adjustment knob 48 is unscrewed from the screw stem 50, the through-hole in the cup-shaped hollow member or housing 12 and base extension 28 is assembled over the screw stem 50, positioning the cup-shaped hollow member or housing 12 in place on the oxygen concentrator 46, and then the dose adjustment knob 48 is replaced by screwing it back onto the screw stem 50. Once the oxygen flow rate is set, the lid 32 is positioned and fastened/locked in place over the cup-shaped hollow member 12, thereby preventing access to the dose adjustment knob.

While the invention is described in connection with certain preferred embodiments, it is understood that it is not intended to limit the invention to those embodiments. Rather, it is intended to cover all alternatives, modifications and equivalents as may be included within the spirit and scope of the invention as defined by the appended claims.

What is claimed is:

1. An assembly for housing and securing an exposed dose adjustment control mechanism of a medical device used to administer a medical therapy, the assembly comprising: a one-piece cup-shaped hollow member having a through-hole in a distal wall; and a substantially planar lid, wherein the cup-shaped hollow member and the lid are held together by a hinge or fastening means, and fastening/locking means, wherein, the dose adjustment control mechanism of the medical device has a user-actuatable element that fits onto a stem secured to the medical device with fastening means having a shape, wherein, the cup-shaped hollow member has a base with a lower base extension molded integrally therewith, and the through-hole extends through both the base and the base extension, wherein, the through-hole adopts the shape of the fastening means, wherein the medical device has an outer surface, a portion of which protrudes relative to surrounding portions, thereby defining a non-planar surface, wherein the base extension conforms to the protruding and surrounding portions of the outer surface allowing it to lie flush or level with the surface of the medical device.

2. The assembly of claim 1, wherein the medical device is an oxygen therapy system.

3. The assembly of claim 2, wherein the oxygen therapy system is an oxygen concentrator.

4. The assembly of claim 1, wherein the user-actuatable element is selected from the group of a knob, a dial, or other rotary or slidable control configured to adjust an operational parameter of the medical device.

5. The assembly of claim 1, wherein the cup-shaped hollow member and the lid are connected by a hinge, which allows for bending of the lid from an 'open' position removed from the cup-shaped hollow member to a 'closed' position on and in alignment with the cup-shaped hollow member.

6. The assembly of claim 5, wherein the assembly is a two-piece assembly, and the hinge is a mechanical hinge.

7. The assembly of claim 5, wherein the assembly is a one-piece assembly, and the hinge is a living hinge.

8. The assembly of claim 1, wherein the inventive assembly is a two-piece assembly in which the cup-shaped hollow member and the lid are connected by fastening means which allow for rotation of the lid from an 'open' position on but misaligned from the cup-shaped hollow member to a 'closed' position on and in alignment with the cup-shaped hollow member.

9. The assembly of claim 8 wherein the fastening means is a bolt with a bolt shaft, which is secured by a nut, wherein rotation of the lid occurs around or about the bolt shaft.

10. The assembly of claim 1, wherein the cup-shaped hollow member has an upper rim having two oppositely extending arms, at least one of which has a through-hole at a distal end thereof.

11. The assembly of claim 6, wherein the cup-shaped hollow member has an upper rim having two oppositely extending arms, one of which has a through-hole at a distal end, wherein the lid has two oppositely disposed extending arms, one of which has a through-hole at a distal end thereof, wherein, when the lid is aligned with the cup-shaped hollow member, the through-holes of both the lid and the cup-shaped hollow member align, and the assembly further comprises a fastening/locking mechanism extending through the aligned through-holes.

12. The assembly of claim 11, wherein the fastening/locking mechanism is selected from the group of keyed or combination lock devices and electronic lock devices.

13. The assembly of claim 7, wherein the cup-shaped hollow member has an upper rim having two oppositely extending arms, one of which has a through-hole at a distal end, wherein the lid has two oppositely disposed extending arms, one of which has a through-hole at a distal end thereof, wherein, when the lid is aligned with the cup-shaped hollow member, the through-holes of both the lid and the cup-shaped hollow member align, and the assembly further comprises a fastening/locking mechanism extending through the aligned through-holes.

14. The assembly of claim 13, wherein the fastening/locking mechanism is selected from the group of keyed or combination lock devices and electronic lock devices.

15. The assembly of claim 8, wherein the cup-shaped hollow member has an upper rim having two oppositely extending arms, each extending arm having a through-hole at a distal end thereof, wherein the lid has two oppositely disposed extending arms, each extending arm also having a through-hole at a distal end thereof, wherein, when the lid is aligned with the cup-shaped hollow member, the through-holes of both the lid and the cup-shaped hollow member align, and the fastening means extend through one set of aligned through-holes and fastening/locking means extend through the other set of aligned through-holes.

16. The assembly of claim 15, wherein the fastening means is a bolt secured by a nut, and wherein the fastening/locking means is selected from the group of keyed or combination lock devices and electronic lock devices.

17. A method for housing and securing exposed dose adjustment control mechanisms of medical devices using the assembly of claim 1, wherein the method comprises:

(a) removing the user-actuatable element from the stem on the medical device used to administer various medical therapies;

(b) positioning the cup-shaped hollow member's through-hole over the stem;

(c) replacing the user-actuatable element by placing it back onto the stem;

(d) setting a prescribed quantity of a medicine or drug using the user-actuatable element; and (e) bending or rotating the lid onto and in alignment with the cup-shaped member and then securing the lid in place on the cup-shaped hollow member, thereby preventing access to the user-actuatable element.

18. The method of claim 17, wherein the user-actuatable element is selected from the group of a knob, a dial, or other rotary or slidable control configured to adjust an operational parameter of the medical device.

19. The method of claim 17, wherein the cup-shaped hollow member and the lid of the assembly are connected by a hinge, which allows for bending of the lid from an 'open' position removed from the cup-shaped hollow member to a 'closed' position on and in alignment with the cup-shaped hollow member.

20. The method of claim 19, wherein the assembly is selected from the group of:

a two-piece assembly in which the hinge is a mechanical hinge; and a one-piece assembly in which the hinge is a living hinge.

21. The method of claim 17, wherein the assembly is a two-piece assembly in which the cup-shaped hollow member and the lid are connected by fastening means which allow for rotation of the lid from an 'open' position on but misaligned from the cup-shaped hollow member to a 'closed' position on and in alignment with the cup-shaped hollow member.

22. A medical device used to administer a medical therapy, which comprises an exposed dose adjustment control mechanism and an assembly for housing and securing the exposed dose adjustment control mechanism, the assembly comprising: a cup-shaped hollow member having a through-hole in a distal wall; and a lid, wherein the cup-shaped hollow member and the lid are held together by a hinge or fastening means, and fastening/locking means, wherein the medical device has an outer surface, a portion of which protrudes relative to surrounding portions, thereby defining a non-planar surface, wherein, the cup-shaped hollow member has a base with a lower base extension molded integrally therewith, the through-hole extending through both the base and the base extension, the base extension conforming to the protruding and surrounding portions of the outer surface of the medical device allowing it to lie flush or level with the surface of the device.

23. The medical device of claim 22, wherein, the dose adjustment control mechanism of the medical device has a user-actuatable element that fits onto a stem secured to the medical device with fastening means having a shape, and wherein, the through-hole adopts the shape of the fastening means.

24. The medical device of claim 22, wherein the cup-shaped hollow member and the lid are connected by a hinge, which allows for bending of the lid from an 'open' position removed from the cup-shaped hollow member to a 'closed' position on and in alignment with the cup-shaped hollow member.

25. The medical device of claim 24, wherein the assembly is a two-piece assembly, and the hinge is a mechanical hinge.

26. The medical device of claim 24, wherein the assembly is a one-piece assembly, and the hinge is a living hinge.

* * * * *